(12) United States Patent
Srimohanarajah et al.

(10) Patent No.: US 11,416,995 B2
(45) Date of Patent: *Aug. 16, 2022

(54) SYSTEMS, DEVICES, AND METHODS FOR CONTACTLESS PATIENT REGISTRATION FOR A MEDICAL PROCEDURE

(71) Applicant: Synaptive Medical Inc., Toronto (CA)

(72) Inventors: Kirusha Srimohanarajah, Toronto (CA); Dorothy Lui, Toronto (CA); Gal Sela, Toronto (CA); Kai Hynna, Toronto (CA); Shysta Ismaili, Toronto (CA); Samson Ng, Toronto (CA); Jakub Jankowski, Toronto (CA)

(73) Assignee: SYNAPTIVE MEDICAL INC., Toronto (CA)

(*) Notice: Subject to any disclaimer, the term of this patent is extended or adjusted under 35 U.S.C. 154(b) by 0 days.

This patent is subject to a terminal disclaimer.

(21) Appl. No.: 17/091,920

(22) Filed: Nov. 6, 2020

(65) Prior Publication Data
US 2021/0056699 A1 Feb. 25, 2021

Related U.S. Application Data

(63) Continuation of application No. 15/794,518, filed on Oct. 26, 2017, now Pat. No. 10,832,408.

(51) Int. Cl.
*G06T 7/00* (2017.01)
*G06T 7/246* (2017.01)
(Continued)

(52) U.S. Cl.
CPC ............ *G06T 7/0014* (2013.01); *A61B 34/20* (2016.02); *G06T 7/248* (2017.01); *G06T 7/80* (2017.01);
(Continued)

(58) Field of Classification Search
None
See application file for complete search history.

(56) References Cited

U.S. PATENT DOCUMENTS

2003/0179856 A1* 9/2003 Mitschke ............... A61B 34/20
378/205
2005/0228266 A1* 10/2005 McCombs ............ A61B 90/39
600/414
(Continued)

FOREIGN PATENT DOCUMENTS

CA 2958013 A1 4/2017
CA 2960528 A1 5/2017
(Continued)

OTHER PUBLICATIONS

H. Mohammadzade and D. Hatzinakos, "Iterative Closest Normal Point for 3D Face Recognition," in IEEE Transactions on Pattern Analysis and Machine Intelligence, vol. 35, No. 2, pp. 381-397, Feb. 2013, doi: 10.1109/TPAMI.2012.107. (Year: 2013).*
(Continued)

*Primary Examiner* — Tahmina N Ansari

(57) ABSTRACT

Methods and apparatuses for performing patient registration. 3D scan data from a 3D scanner, preoperative image data, first tracking data from a first tracking system, and second tracking data from a second tracking system are mapped to a common coordinate space. The 3D scan data and the first tracking data are mapped to each other using a transformation that is determined based on a calibration relating the 3D scan coordinate space and the tracking coordinate space. The 3D scan data and the preoperative image data are mapped to each other using a surface matching algorithm. The first tracking data and the second tracking data are mapped to each other based on tracking of the patient reference device.

20 Claims, 10 Drawing Sheets

(51) Int. Cl.
*G06T 11/00* (2006.01)
*A61B 34/20* (2016.01)
*G16H 20/40* (2018.01)
*G06T 7/80* (2017.01)
*G16H 40/60* (2018.01)
*G16H 30/40* (2018.01)
*G16H 40/40* (2018.01)

(52) U.S. Cl.
CPC .......... *G06T 11/005* (2013.01); *G16H 20/40* (2018.01); *G16H 30/40* (2018.01); *G16H 40/40* (2018.01); *G16H 40/60* (2018.01); *G06T 2200/04* (2013.01); *G06T 2207/30208* (2013.01)

(56) References Cited

U.S. PATENT DOCUMENTS

| | | | | |
|---|---|---|---|---|
| 2012/0029387 | A1* | 2/2012 | Wei | A61B 90/36 600/587 |
| 2017/0238998 | A1* | 8/2017 | Srimohanarajah | A61B 34/10 |
| 2017/0348061 | A1* | 12/2017 | Joshi | A61B 34/10 |
| 2018/0256264 | A1* | 9/2018 | McLachlin | A61B 90/39 |
| 2019/0130568 | A1* | 5/2019 | Srimohanarajah | G06T 7/0014 |

FOREIGN PATENT DOCUMENTS

| | | |
|---|---|---|
| WO | 2016205915 A1 | 12/2016 |
| WO | 2017011892 A1 | 1/2017 |

OTHER PUBLICATIONS

Yaorong Ge, Calvin R. Maurer Jr., and J. Michael Fitzpatrick "Surface-based 3D image registration using the iterative closest-point algorithm with a closest-point transform", Proc. SPIE 2710, Medical Imaging 1996: Image Processing, https://doi.org/10.1117/12.237938 (Year: 1996) Apr. 16, 1996.

U.K. Intellectual Property Office, "Search Report" for corresponding GB Application No. GB1817325.2. dated Apr. 25, 2019.

Search report issued by the Intellectual Property Office of the UK in relation to GB Application No. GB1817325.2 dated Nov. 30, 2021, 2 pgs.

* cited by examiner

SYSTEMS, DEVICES, AND METHODS FOR CONTACTLESS PATIENT REGISTRATION FOR A MEDICAL PROCEDURE

CROSS-REFERENCE TO RELATED APPLICATION

This application is a continuation of U.S. patent application Ser. No. 15/794,518 filed Oct. 26, 2017, titled PATIENT REGISTRATION SYSTEMS, DEVICES, AND METHODS FOR A MEDICAL PROCEDURE, the contents of which are hereby expressly incorporated into the present application by reference in their entirety.

FIELD

The present disclosure relates to apparatuses and methods for registration of a patient for a medical procedure. In particular, the present disclosure relates to registration of a patient using information from a 3D scanner and a tracking system.

BACKGROUND

During an image-guided medical procedure, such as in a neurosurgical procedure, navigation systems require a registration to transform between the physical position of the patient in the operating room and the volumetric image set being navigated to. Volumetric images may include magnetic resonance (MR) images or computed tomography (CT) images, for example.

Conventionally, this registration is performed using a pre-operative scan (e.g., MR or CT scan), prior to the medical procedure. During the pre-operative scan, fiducial registration takes place, using fiducial markers placed on landmarks on the face. These fiducial markers are often difficult to adhere to onto the desired facial features and may shift or fall off, resulting in inaccurate scans or a need for repeated scans.

Another conventional approach is to perform registration using touch points (e.g., either fiducial or anatomic points) or surface trace, in which fiducial markers may not be needed. However, touch point or surface trace collection is subject to user variability. Further, touch point or surface trace registration involves contact with the patient (e.g., using a physical stylus), which can deform or deflect patient skin position and thus introduce error.

Other common limitations of the conventional approaches to registration discussed above include a stylus that needs to remain visible to the tracking system, which may not necessarily be possible depending on a patient's surgical position or may introduce surgical restrictions that need to be accounted in planning, and error accumulation where touch point or tracing collection is of low quality resulting in error propagation through subsequent steps of the registration. Further, using the conventional methods, if registration is lost, re-registration is difficult to be completed again during the surgical procedure.

SUMMARY

In various examples disclosed herein, a contactless approach for patient registration is described. A patient may be registered for a medical procedure using example apparatuses and methods disclosed herein.

In some examples, a method of registering a patient for a medical procedure using a medical navigation system is described. The method includes obtaining 3D scan data from a 3D scanner. The 3D scan data is obtained for a patient surface relevant to the medical procedure, and the 3D scan data is in a 3D scan coordinate space. The method also includes obtaining preoperative image data of the patient surface. The preoperative image data is in a preoperative image coordinate space. The method also includes obtaining first tracking data from a first tracking system. The first tracking data is obtained for a patient reference device, and the first tracking data is in a first tracking coordinate space. The method also includes obtaining second tracking data from a second tracking system. The second tracking data is obtained for the patient reference device, and the second tracking data is in a second tracking coordinate space. The method also includes mapping the 3D scan data, preoperative image data and second tracking data to a common coordinate space. The mapping includes mapping the 3D scan data and the first tracking data to each other using a transformation. The transformation is determined based on a calibration relating the 3D scan coordinate space and the tracking coordinate space. The mapping also includes mapping the 3D scan data and the preoperative image data to each other using a surface matching algorithm. The mapping also includes mapping the first tracking data and the second tracking data to each other based on tracking of the patient reference device.

In some examples, a medical navigation system is described. The system includes a 3D scanner coupled with a first tracking system, a second tracking system, a patient reference device, and a controller in communication with the 3D scanner, the first tracking system and the second tracking system. The controller includes a processor configured to receive 3D scan data from the 3D scanner. The 3D scan data is obtained for a patient surface relevant to the medical procedure, and the 3D scan data is in a 3D scan coordinate space. The processor is also configured to retrieve preoperative image data of the patient surface. The preoperative image data is in a preoperative image coordinate space. The processor is also configured to receive first tracking data from the first tracking system. The first tracking data is obtained for the patient reference device, and the first tracking data is in a first tracking coordinate space. The processor is also configured to receive second tracking data from the second tracking system. The second tracking data is obtained for the patient reference device, and the second tracking data is in a second tracking coordinate space. The processor is also configured to map the 3D scan data, preoperative image data and second tracking data to a common coordinate space. The mapping includes mapping the 3D scan data and the first tracking data to each other using a transformation. The transformation is determined based on a calibration relating the 3D scan coordinate space and the tracking coordinate space. The mapping also includes mapping the 3D scan data and the preoperative image data to each other using a surface matching algorithm. The mapping also includes mapping the first tracking data and the second tracking data to each other based on tracking of the patient reference device.

In some examples, the present disclosure describes a patient reference device for registering a patient for a medical procedure. The patient reference device includes a body having a first side and an opposing second side. The patient reference device also includes a first plurality of tracking markers supported on the first side and a second plurality of tracking markers supported on the second side. The tracking markers are trackable by a tracking system. The patient reference device also includes at least one feature on the first side detectable by a 3D scanner. The at least one feature is configured for calibrating the tracking system with the 3D scanner.

BRIEF DESCRIPTION OF THE DRAWINGS

Reference will now be made, by way of example, to the accompanying drawings which show example embodiments of the present application, and in which.

Similar reference numerals may have been used in different figures to denote similar components.

DESCRIPTION OF EXAMPLE EMBODIMENTS

Figure 1:
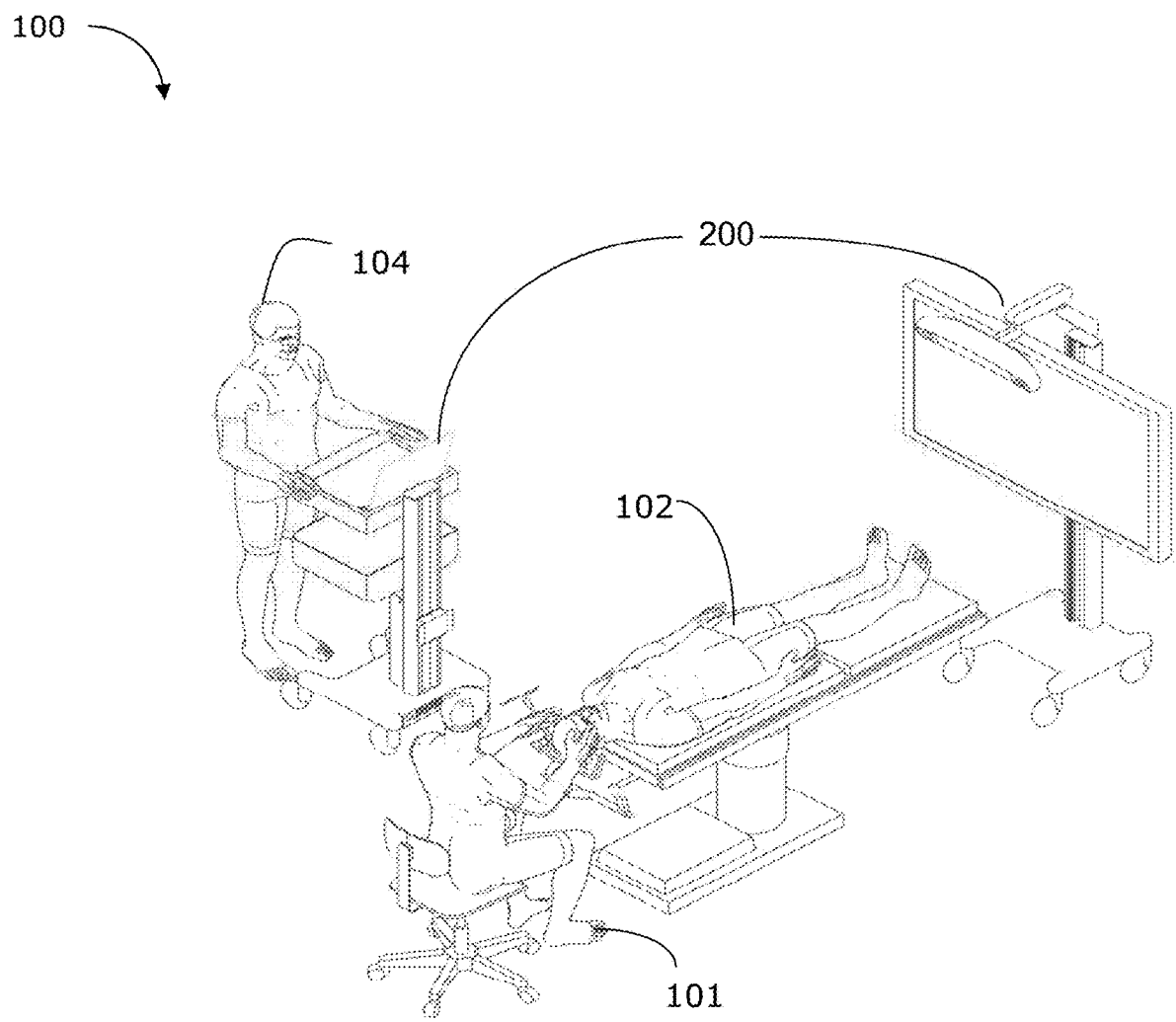
FIG. 1 shows an example operating room setup for an image guided medical procedure.

The systems and methods described herein may be useful for various surgical or non-surgical medical procedures, including spinal procedures, neural procedures, orthopaedic procedures or biopsy procedures. The systems and methods described herein may be useful for co-registration of preoperative and intraoperative image data, together with tracking data. The present disclosure may also be useful for co-registration of two or more sets of intraoperative image data, or two or more sets of preoperative image data, together with tracking data. Although described in the context of a neural medical procedure, the teachings of the present disclosure may be applicable to other conditions or fields of medicine. It should be noted that while the present disclosure describes examples in the context of neural surgery, the present disclosure may be applicable to other procedures that may benefit from touchless patient registration.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" or "example" means "serving as an example, instance, or illustration," and should not be construed as preferred or advantageous over other configurations disclosed herein.

As used herein, the terms "about", "approximately", and "substantially" are meant to cover variations that may exist in the upper and lower limits of the ranges of values, such as variations in properties, parameters, and dimensions. In one non-limiting example, the terms "about", "approximately", and "substantially" mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings:

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

As used herein the phrase "preoperative" refers to an action, process, method, event or step that occurs prior to the start of a medical procedure. Preoperative, as defined herein, is not limited to surgical procedures, and may refer to other types of medical procedures, such as diagnostic and therapeutic procedures. Planning a medical procedure may be considered to be preoperative.

Some embodiments of the present disclosure may relate to minimally invasive medical procedures that are performed via an access port or retractor tube, whereby surgery, diagnostic imaging, therapy, or other medical procedures (e.g., minimally invasive medical procedures) are performed based on access to internal tissue through the access port or retractor tube.

In FIG. 1, an operating room (OR) environment 100 is shown, which may be used to support navigated image-guided surgery. As shown in FIG. 1, a surgeon 101 conducts a medical procedure, for example a neurosurgery procedure, on the patient 102 in the OR environment 100. A medical navigation system 200 (described further below) may include an equipment tower, tracking system and display(s) to provide image guidance and/or tracking information, to assist the surgeon 101 during the procedure. An operator 104 may also be present to operate and control the medical navigation system 200, as well as provide other assistance during the medical procedure.

Figure 2:
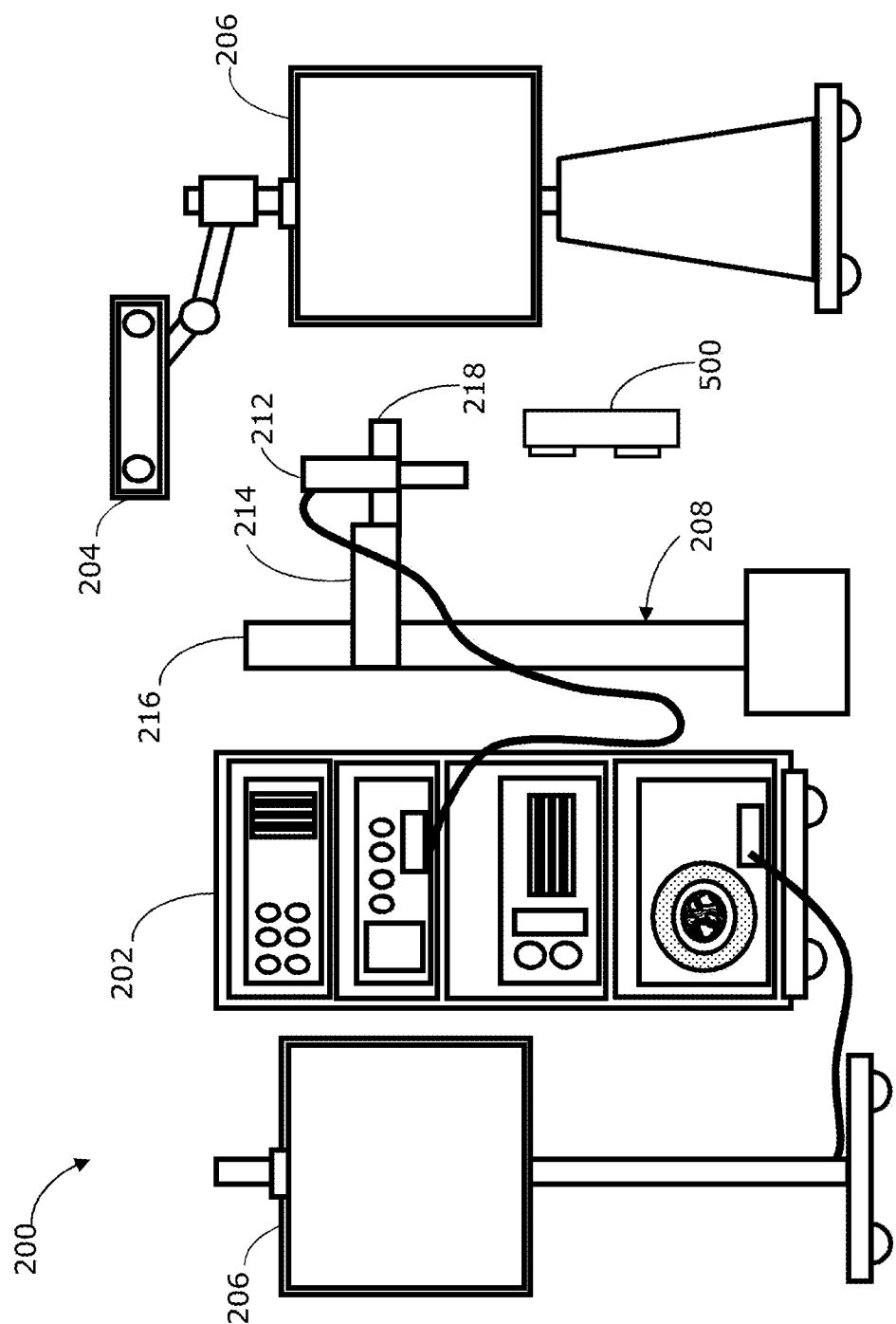
FIG. 2 shows an example navigation system suitable for image guided medical procedures.

FIG. 2 is a diagram illustrating example components of the navigation system 200. The navigation system 200 may provide intraoperative navigation assistance for various medical procedures, including neural procedures, spinal procedures, or other surgical or non-surgical procedures. In the example shown, the navigation system 200 includes an equipment tower 202, a tracking system 204, one or more displays 206, and a positioning system 208. Although described as part of the navigation system 200, in some examples one or more components described with reference to and shown in FIG. 2 may be separate from the navigation system 200 (e.g., the tracking system 204 may be a separate system that operates in conjunction with the navigation system 200). The tracking system 204 may include an optical tracking device, tracking camera, video camera, infrared camera, or any other suitable camera or scanner based system. The tracking system 204 may be used to track markers (described further below) to obtain tracking data, which may be used to determine the position and orientation of a tracked object.

The positioning system 208 in this example includes an automated mechanical arm 214 (also referred to as a robotic arm or automated arm 214), a lifting column 216 and an end effector 218. The lifting column 216 is connected to a frame of the positioning system 208. In the example of FIG. 2, the proximal end of the automated arm 214 is connected to the lifting column 216. In other examples, the automated arm 214 may be connected to a horizontal beam, which is then either connected to the lifting column 216 or directly to the frame of the positioning system 208. The automated arm 214 may have multiple joints, for example to enable five, six or seven degrees of freedom.

The end effector 218 is attached to the distal end of the automated arm 214. The end effector 218 may accommodate a plurality of instruments or tools for the medical procedure. In FIG. 2, the end effector 218 is shown as holding an intraoperative imaging system 212 such as an optical scope and two-dimensional (2D) camera, however it should be noted that any alternate devices may be used with the end effector 218 including a wide field camera, microscope and Optical Coherence Tomography (OCT), video camera, or other imaging instruments, as well as devices other than an imaging system 212. In some examples, the intraoperative imaging system 212 may include a wide field camera in connection with an external scope, which may be held together by a single end effector 218. In another example, multiple end effectors 218 may be attached to the distal end of the automated arm 214, for example to hold different imaging systems to enable switching among multiple imaging modalities. In some examples, different end effectors 218 may provide different ranges of control (e.g., a micro-control effector may be used to hold a tool requiring finer control, such as a laser-based ablation system).

The positioning system 208 may receive input information about the spatial position and orientation of the automated arm 214, end effector 218 and/or imaging system 212, and any tracked object. The position and orientation of the tracked object may be determined by the tracking system 204 by detection of one or more markers on the object. The position and orientation of the automated arm 214, end effector 218 and/or imaging system 212 may be determined by the tracking system 204 by detection of markers provided on the automated arm 214, end effector 218 and/or imaging system 212. In some examples, position sensors on the automated arm 214 may provide information about the position and orientation of the automated arm 214, and the position and orientation of the end effector 218 and/or imaging system 212 may be determined based on the known position and orientation of the end effector 218 and/or imaging system 212 relative to the automated arm 214.

The positioning system 208 may work in conjunction with the tracking system 204 to position the intraoperative imaging system 212 to maintain alignment with an object of interest, such as aligned with the passage of an access port. For example, the positioning system 208 may compute the desired joint positions for the automated arm 214 so as to manoeuvre the end effector 218 to a predetermined spatial position and orientation relative to the tracked object. This predetermined relative spatial position and orientation may be designated as the "Zero Position", such as where the field-of-view (FOV) of the imaging device 212 is aligned with the tracked object.

Further, the positioning system 208, the tracking system 204 and the automated arm 214 may form a feedback loop. This feedback loop may work to keep the tracked object in constant view and focus of the imaging device 212 (e.g., where the end effector 218 holds the imaging device 212), as the tracked object may move during the procedure. The positioning system 208 may also include an input mechanism, such as a foot pedal, which may be activated to control the automated arm 214 to automatically align the imaging device 212 (e.g., held by the end effector 218) with the tracked object.

A handheld apparatus 500 (described further below, with reference to FIGS. 5A-5C) may be used to capture intraoperative 3D image data about the object of interest, and may also provide additional tracking information, such as to track a patient reference device (not shown). The apparatus 500 may be used to perform patient registration, as discussed further below. In some examples, the apparatus 500 may be referred to as a 3D scanner and tracking camera, 3D scanner with coupled tracking camera, registration scanner or rapid registration scanner.

The image data captured by the intraoperative imaging system 212 may be displayed on one or more of the display(s) 206. The display(s) 206 may also display other image data, such as preoperative image data (e.g., MR or CT image data) or 3D image data, as well as other navigation information.

Figure 3:
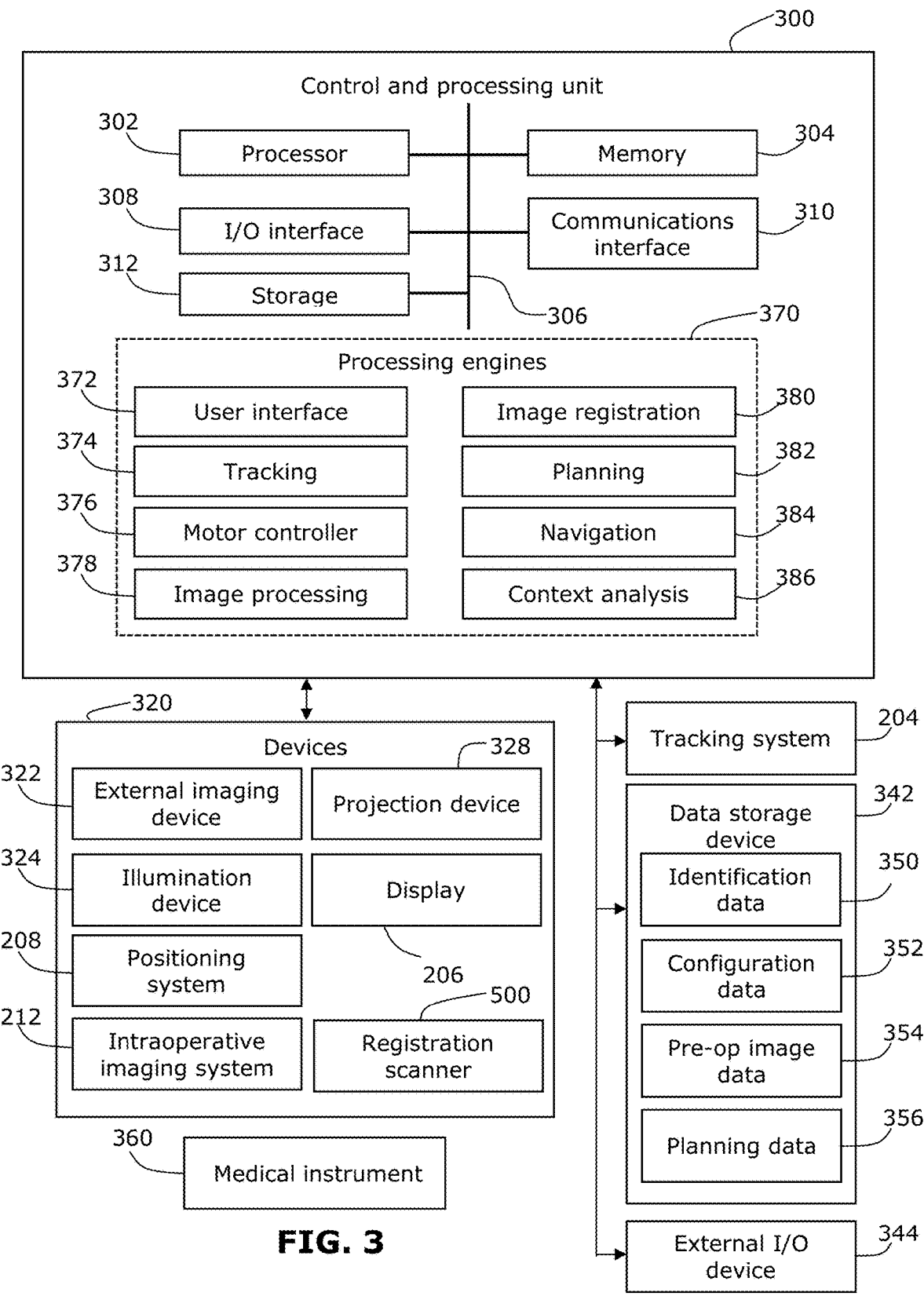
FIG. 3 is a block diagram illustrating an example control and processing system that may be used in the navigation system of FIG. 2.

In FIG. 3, a block diagram is shown illustrating a control and processing unit 300 that may be used in the medical navigation system 200 (e.g., as part of the equipment tower 202). Although FIG. 3 shows and is described with reference to a single instance of each component, in some examples there may be multiple instances of certain components.

As shown in FIG. 3, in an example, the control and processing system 300 may include a processor 302, a memory 304, a system bus 306, an input/output interface 308, a communications interface 310, and a storage device 312. The control and processing system 300 may be interfaced with other external devices/systems, such as the tracking system 204, a data storage device 342, and an external input and output device 344, which may include, for example, one or more of a display, keyboard, mouse, sensors attached to medical equipment, foot pedal, microphone or speaker. The data storage device 342 may be any suitable data storage device, such as a local or remote computing device (e.g. a computer, hard drive, digital media device, or server) having a database stored thereon.

In the example shown in FIG. 3, the data storage device 342 includes identification data 350 for identifying one or more medical instruments 360 and configuration data 352 that may associate configuration parameters with one or more of the medical instrument(s) 360. The data storage device 342 may also include preoperative image data 354 and/or medical procedure planning data 356. Although the data storage device 342 is shown as a single device in FIG. 3, in some examples the data storage device 342 may be provided as multiple storage devices.

The medical instrument 360 may be identifiable by the control and processing unit 300. The medical instrument 360 may be connected to and controlled by the control and processing unit 300, or the medical instrument 360 may be operated or otherwise employed independent of the control and processing unit 300. The tracking system 204 may be employed to track one or more of the medical instrument(s)

360. For example, one or more tracking markers may be provided on the medical instrument 360, or the medical instrument 360 may be coupled to a tracked object (e.g., a trackable sheath or a trackable frame).

The control and processing unit 300 may also interface with one or more devices 320, which may include configurable devices. The control and processing unit 300 may intraoperatively reconfigure one or more of such devices 320 based on configuration parameters obtained from the configuration data 352. Example devices 320 include an external imaging device 322, an illumination device 324, the positioning system 208, the intraoperative imaging system 212, a projection device 328, the display 206, and the apparatus 500 (referred to also as registration scanner).

The control and processing unit 300 may implement examples described herein, via the processor 302 and/or memory 304. For example, the functionalities described herein can be implemented via hardware logic in the processor 302 and/or using instructions stored in the memory 304, as one or more processing modules or engines 370. Example processing engines 370 include, but are not limited to, a user interface engine 372, a tracking engine 374, a motor controller 376, an image processing engine 378, an image registration engine 380, a procedure planning engine 382, a navigation engine 384, and a context analysis engine 386. While the example processing engines 370 are shown separately in FIG. 3, in some examples the processing engines 370 may be collectively stored as one or more sets of computer-readable instructions (e.g., stored in the memory 304). In some examples, two or more processing engines 370 may be used together to perform a function.

It is to be understood that the system is not intended to be limited to the components shown in FIG. 3. One or more components of the control and processing system 300 may be provided as an external component or device. For example, the navigation module 384 may be provided by an external navigation system that is integrated with the control and processing system 300

In some examples, the navigation system 200, which may include the control and processing unit 300, may provide tools to the surgeon that may help to improve the performance of the medical procedure and/or post-operative outcomes. In addition to neural procedures, the navigation system 200 can also be used in the context of an orthopaedic procedure or a spinal procedure, as well as medical procedures on other parts of the body such as breast biopsies, liver biopsies, and others. While some examples are described herein, examples of the present disclosure may be applied to any suitable medical procedure.

Generally, the intraoperative image data obtained by the intraoperative imaging device 212 is in a coordinate space different from and independent of the coordinate space of the preoperative image data (e.g., MR or CT image data). More generally, different sets of image data may be in different coordinate spaces, even where the image data are all obtained intraoperatively or all obtained preoperatively, and even where the image data are obtained using the same imaging modality. As well, tracking data obtained by the tracking system 204 is in a coordinate space different from and independent of the image coordinate spaces. Data obtained by the apparatus 500 (e.g., 3D scan data and another set of tracking data) generally are also in a different coordinate space.

Co-registration of these different sets of data may be achieved by performing a transformation mapping to map the sets of data into a common coordinate space. This mapping may also be referred to as co-registration of the sets of data, so that two or more of these data sets can be presented together (e.g., using visual overlays) to provide navigation assistance to the surgeon during the medical procedure.

In some examples, the transformation mapping may be used to co-register two or more sets of intraoperative image data. For example, intraoperative MR or CT image data may be co-registered with intraoperative optical image data and/or intraoperative 3D scan data. In some examples, two or more sets of preoperative image data may be co-registered, for example co-registration of MR and CT image data. In some examples, preoperative data may be co-registered with intraoperative data. In some examples, the transformation mapping may be used to co-register two or more sets of image data obtained using the same imaging modality (e.g., between two sets of optical image data, or two sets of intraoperative CT image data). The image data may be further co-registered with the tracking data in a common coordinate space.

The common coordinate space may result from co-registration of one or more actual coordinate spaces and/or one or more virtual coordinate spaces. An actual coordinate space contains actual objects that exist in physical space and a virtual coordinate space contains virtual objects that are computer-generated in a virtual space.

Figure 4:
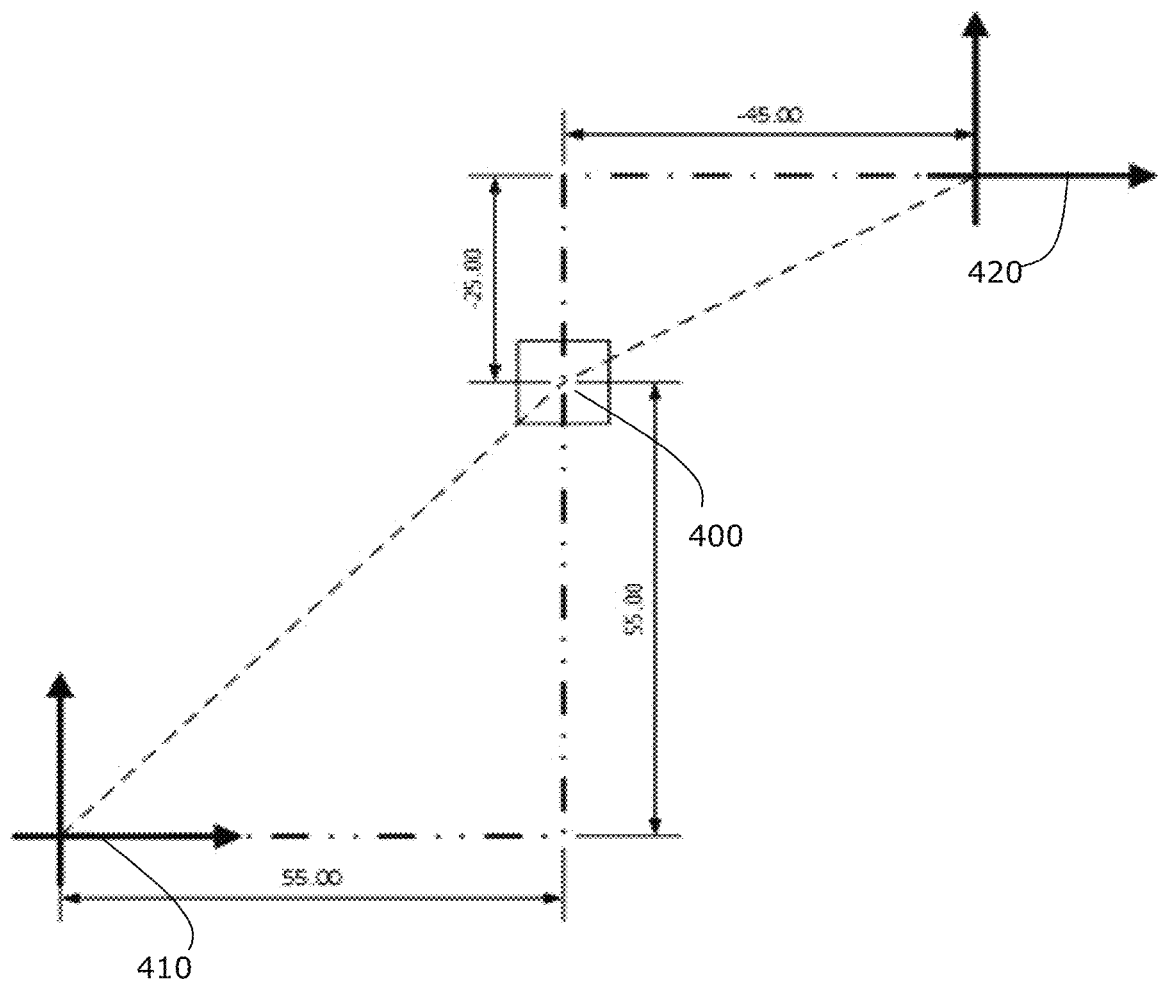
FIG. 4 is a diagram illustrating co-registration of two coordinate spaces.

FIG. 4 illustrates a simplified example of how two coordinate spaces may be co-registered by performing a transformation mapping, based on a common reference coordinate. For simplicity, although FIG. 4 illustrates co-registration of 2D coordinate spaces, co-registration may be performed for 3D coordinate spaces, including a depth dimension.

In the example shown, a common reference coordinate 400 has a defined position and orientation in first and second coordinate spaces 410, 420. In the context of a medical procedure, the common reference coordinate 400 may be a fiducial marker or anatomical reference. In some examples, the common reference coordinate 400 may be provided by a patient reference device, described further below. Co-registration of different pairs of coordinate spaces may be performed using different common reference coordinates, to arrive at a common coordinate space for all data sets. For example, 3D scan data may be co-registered to tracking data using a first common reference coordinate, then the 3D scan data may be co-registered to preoperative image data using a second common reference coordinate, and the result is that the 3D scan data, tracking data and preoperative image data are all co-registered to a common coordinate space.

For simplicity, co-registration of two coordinate spaces is now described with reference to FIG. 4. The position and orientation of the common reference coordinate 400 is used to correlate the position of any point in the first coordinate space 410 to the second coordinate space 420, and vice versa. The correlation is determined by equating the locations of the common reference coordinate 400 in both spaces 410, 420 and solving for a transformation variable for each degree of freedom defined in the two coordinate spaces 410, 420. These transformation variables may then be used to transform a coordinate element of a position in the first coordinate space 410 to an equivalent coordinate element of a position in the second coordinate space 420, and vice versa.

In FIG. 4, the common reference coordinate 400 has a coordinate position (x1, y1) determined in the first coordinate space 410 and a coordinate position (x2, y2) in the second coordinate space 420. In the example shown, (x1, y1)=(55, 55) and (x2, y2)=(−45, −25).

Utilizing transformation equations, any point in the first coordinate space 410 may be related to the second coordinate space 420 via translation variables (xT, yT), as shown below:

x1=x2+xT
y1=y2+yT

Using the coordinate positions of the common reference coordinate 400, the transformation variables may be solved as follows:

55=−45+yT
100=yT
55=−25+xT
80=xT

The transformation variables may then be used to transform any coordinate point in the first coordinate space 410 to the second coordinate space 420, and vice versa, thereby co-registering the coordinate spaces 410, 420. For transformation between 3D coordinate spaces, similar calculations may be performed for position (x, y, z- coordinates) as well as for orientation (pitch, yaw, roll). In general, a transformation mapping may be performed to register two or more coordinate spaces with each other. Where there are more than two coordinate spaces to be co-registered, the transformation mapping may include multiple mapping steps.

In examples disclosed herein, methods and apparatuses for contactless patient registration are described. Generally, obtaining a 3D scan of a patient's surface provides a larger and/or denser set of point information than using touch points or surface trace. A 3D scanner can be used to capture a full or nearly full array scan of a patient's surface and the 3D scan data may be provided as a 3D point cloud. Further, 3D scan data can directly capture depth information about a scanned surface, which may be used to generate a 3D surface contour. The 3D scan data may be co-registered with preoperative image data (e.g., MR or CT data) by mapping the 3D surface contour (generated from the 3D scan data) to a 3D extracted surface (generated from the preoperative image data). However, a reference coordinate is required to co-register the 3D scan data with the tracking data.

Figure 5A:
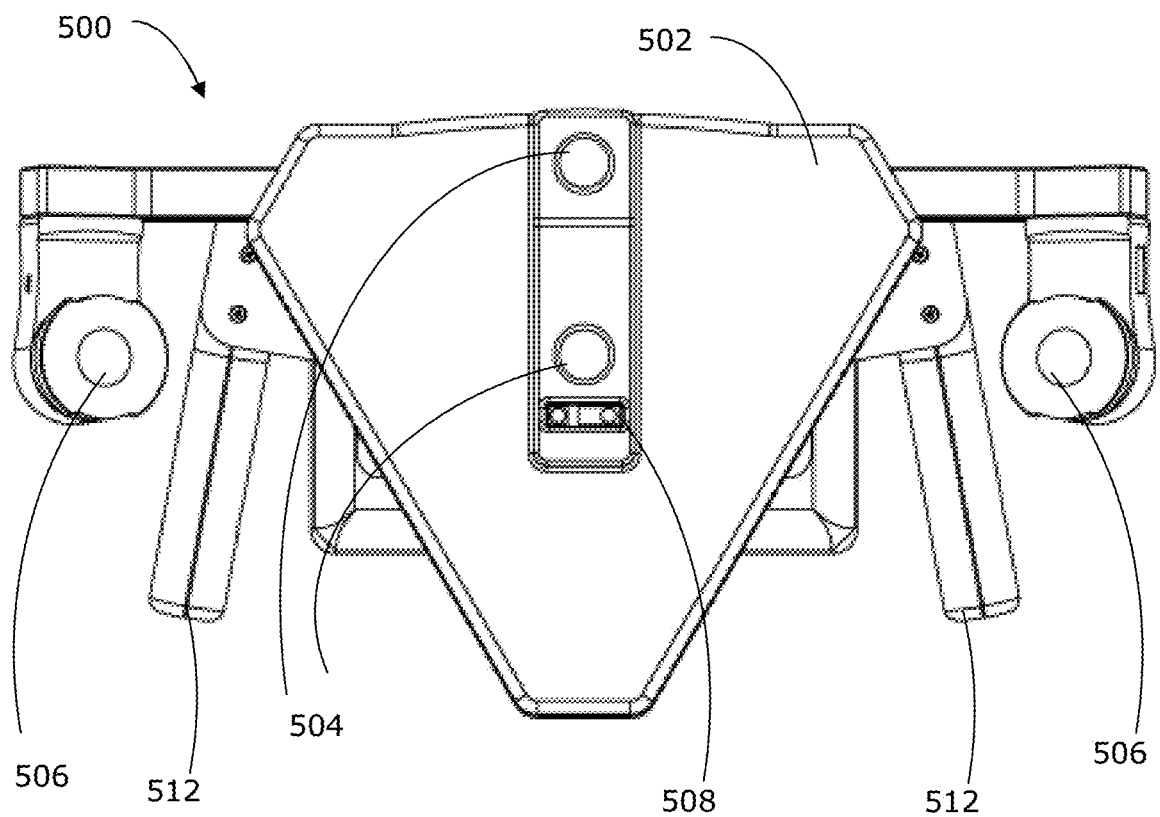
FIG. 5A is a front view of an example apparatus for obtaining 3D scan data and tracking data, for patient registration.
Figure 5B:
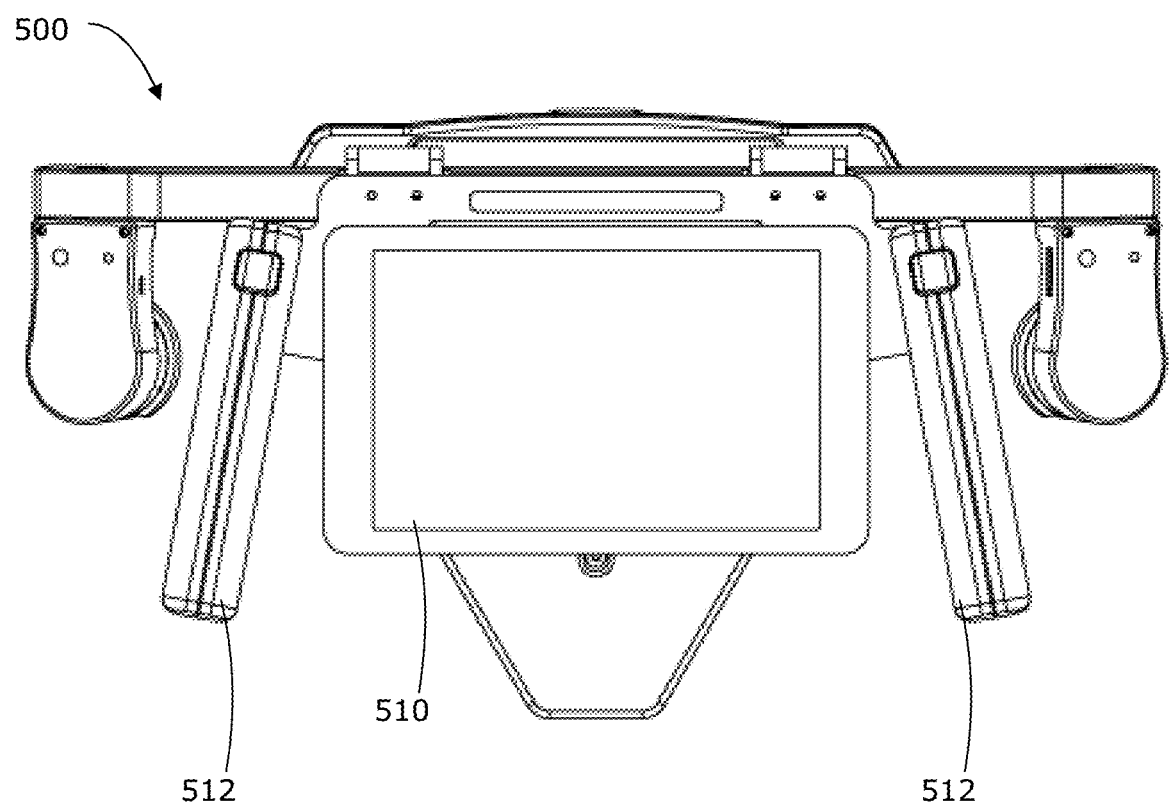
FIG. 5B is a back view of the example apparatus of FIG. 5A.
Figure 5C:
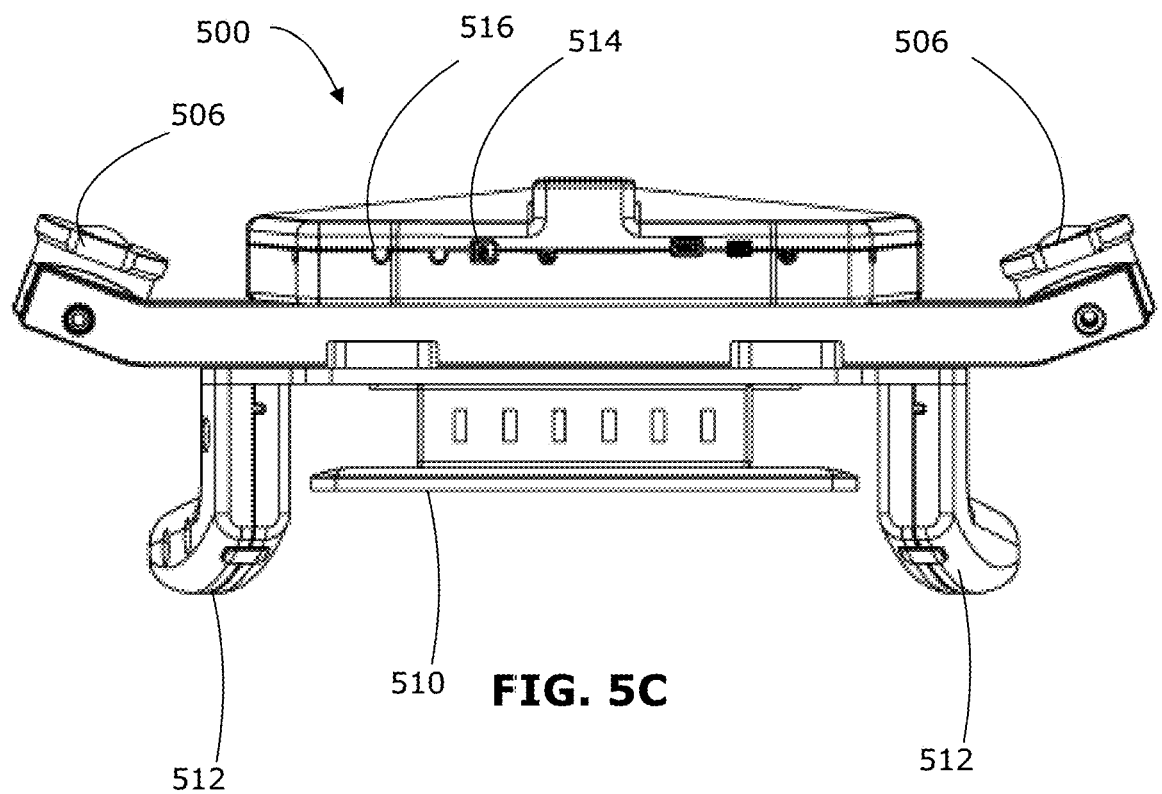
FIG. 5C is a top view of the example apparatus of FIG. 5C.

In examples disclosed herein, the co-registration of 3D scan data with tracking data is performed by providing an additional set of tracking data. FIGS. 5A, 5B and 5C show front, back and top views, respectively, of an example apparatus 500 that may be used to perform patient registration. For clarity, in the following discussion the tracking system provided on the apparatus 500 is referred to as the first tracking system or registration tracking system, and provides first tracking data; the tracking system 204 for tracking the overall medical procedure is referred to as the second tracking system or overall tracking system, and provides second tracking data.

The apparatus 500 includes a 3D scanner 502, having at least two cameras 504 for capturing 3D scan data. The 3D scan data may be captured as a set of points or a mesh. The 3D scan data may be provided as a 3D point cloud. The 3D scanner 502 may be any suitable system for obtaining a 3D scan, for example an infrared scanner or a structured light scanner. The 3D scanner 502 may also serve to obtain optical images. The 3D scanner 502 may also have a distance sensor 508 (e.g., an infrared range sensor) for detecting the distance between the apparatus 500 and an object such as the patient surface.

The apparatus 500 also includes a first tracking system 506, which in this case includes two tracking cameras for capturing first tracking data. The first tracking system 506 may operate similarly to the second tracking system 204. For example, the first tracking system 506 may use infrared cameras to track tracking markers that are reflective spheres. The first tracking system 506 may be any suitable tracking system, and may track any suitable passive or active tracking markers. The first tracking system 506 may operate similarly to or differently from the second tracking system 204. It may be useful for the first tracking system 506 and the second tracking system 204 to operate using similar tracking methods (e.g., both being infrared tracking systems) so that the same tracking markers (e.g., passive reflective spheres) on a patient reference device can be tracked by both the first and second tracking systems 506, 204. The first tracking system 506 may be coupled to the 3D scanner 502 in a fixed relationship. The fixed relationship between the first tracking system 506 and the 3D scanner 502 may be determined via calibration, as discussed further below.

The apparatus 500 may also include a display 510. The display 510 may provide a real-time view of the capture area of the 3D scanner 502, and may function as a viewfinder for the 3D scanner 502. The display 510 may provide feedback information to guide capture of 3D scan data, as discussed further below.

The apparatus 500 may also include one or more handles 512 for holding the apparatus 500.

The apparatus 500 may also include at least one communication port 514 (e.g., a universal serial bus (USB) port) to enable communication between the apparatus 500 and one or more other components of the navigation system 200, such as the control and processing unit 300. The communication port 514 may also be used to connect the apparatus 500 to an external power source. In some examples, the apparatus 500 may include its own power source (e.g., batteries) so that connection to an external power source is not required. In some examples, the apparatus 500 may include a rechargeable battery that may be charged by the external power source. In some examples, the communication port 514 may not be required, such as where the apparatus 500 includes a wireless communication interface for wireless communication with the navigation system 200, or such as where the apparatus 500 has a permanent cable for communication with the navigation system 200.

The apparatus 500 may also include a distance indicator 516 (e.g., a LED) which may cooperate with the distance sensor 508 to indicate when the apparatus 500 is at a suitable distance from a scanning target. For example, the distance indicator 516 may light up, change colours or otherwise provide a visual indication when the distance sensor 508 detects that the apparatus 500 is at a suitable distance from the scanning target (e.g., patient surface). The suitable distance may be a range of distances at which the 3D scanner 502 can accurately capture 3D scan data. In some examples, a non-visual indication (e.g., audio indication or tactile indication) may be provided instead.

The apparatus 500 may optionally include a processing unit, which may perform some or all of the data processing and calculations described below. In other examples, the apparatus 500 may not include a processing unit, but may instead communicate with the control and processing unit 300 of the navigation system 200.

Using the apparatus 500, a user (e.g., surgeon 101 or assistant 104) can simultaneously capture 3D scan data of the patient surface (e.g., patient's face or head, in the case of a neural procedure) and capture first tracking data of a patient reference device. Because the relationship between the 3D scanner 502 and the first tracking system 506 is fixed and known (e.g., via calibration), and because the patient reference device serves as a common reference coordinate for the first tracking system 506 and the second (i.e., overall) tracking system 204, the 3D scan data may be mapped to the second tracking data.

Figure 6:
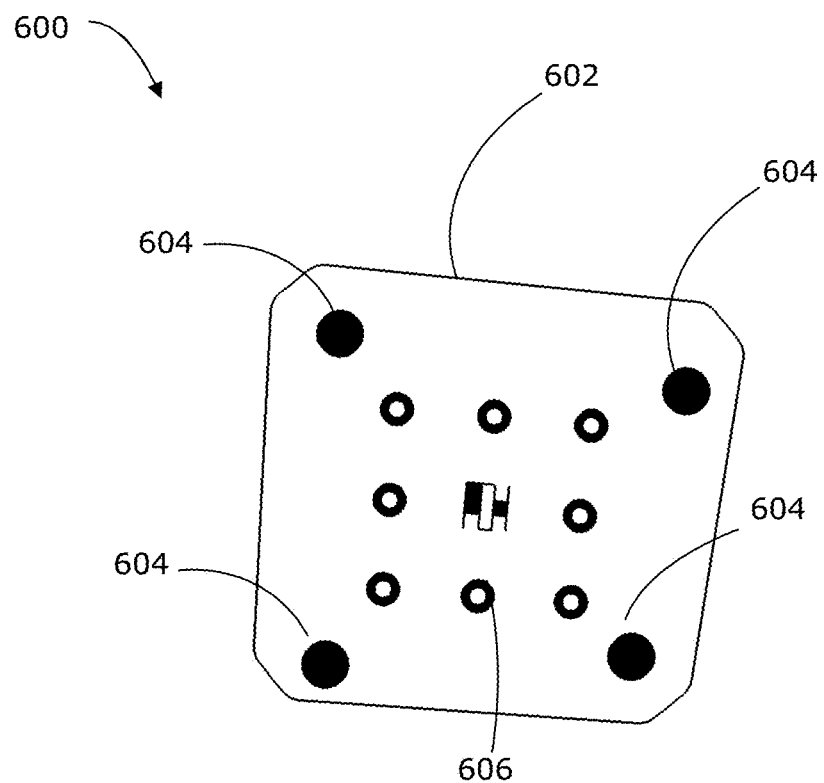
FIG. 6 is an example calibration device for calibrating the example apparatus of FIG. 5A.

The relationship between the 3D scanner 502 and the first tracking system 506 may be determined via calibration, for example using a calibration object such as the calibration object 600 shown in FIG. 6. The example calibration object 600 includes a body 602, supporting tracking markers 604 detectable by the first tracking system 506, and an optical pattern 606 detectable by the 3D scanner 502. There may be at least three tracking markers 604, and FIG. 6 shows an example with four tracking markers 604 placed near the four corners of the body 602. The optical pattern 606 in this example includes a grid of circles. In some examples, the optical pattern 606 may be 3D. The configuration of the tracking markers 604 and the optical pattern 606 relative to each other is fixed and known.

Using the apparatus 500, 3D scan calibration data is obtained by the 3D scanner 502 simultaneously with first tracking calibration data obtained by the first tracking system 506. By "simultaneously", it is meant that the 3D scan calibration data is obtained at substantially the same moment in time as the first tracking calibration data. Because the configuration of the tracking markers 604 and the optical pattern 606 relative to each other is fixed and known, a transformation can be calculated to map the 3D scan calibration data and the first tracking calibration data to each other. This transformation may be calculated (e.g., as a transformation matrix) and stored by the on-board processing unit of the apparatus 500 or by the control and processing unit 300 of the navigation system 200. This transformation can be used to later map 3D scan data obtained by the 3D scanner 502 to first tracking data obtained by the first tracking system 506.

This calibration may be performed only as required, for example if the apparatus 500 is dropped or during normal maintenance. It may not be necessary to perform calibration prior to each patient registration, but instead it may be assumed that the previous calibration is still valid.

In some examples, calibration by the user may not be required at all. For example, calibration of the 3D scanner 502 and first tracking system 506 may be performed by the manufacturer or vendor of the apparatus 500 and the transformation may be already stored on the apparatus 500.

Figure 7:
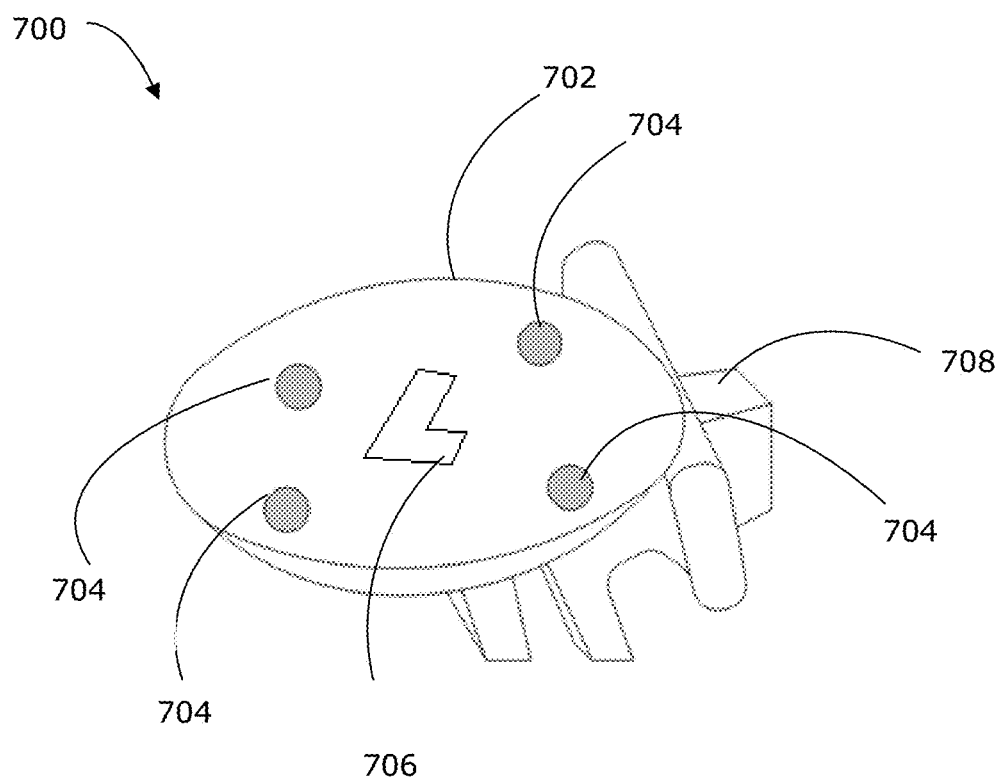
FIG. 7 is an example patient reference device for performing patient registration.

A patient reference device, such as the patient reference device 700 shown in FIG. 7, may be used to perform registration of the patient. In the example shown, the patient reference device 700 includes a body 702 supporting tracking markers 704 on both a first side and an opposing second side. The body 702 may be constructed in such a way as to minimize interference with detection of the tracking markers 704. For example, the body 702 may be constructed to have a matte finish, or low-reflective or non-reflective finish. The body 702 may also include a feature 706, such as a 3D feature and/or 2D optical pattern, detectable by the 3D scanner 502. Where the patient reference device 700 includes the feature 706 at a fixed and known relationship to the tracking markers 704, the patient reference device 700 may be used for calibration of the 3D scanner 502 and the first tracking system 506, and a separate calibration object may not be needed. The body 702 may be connected (e.g., at a connection point 708) to a connector (e.g., rigid arm) to rigidly and fixedly connect the patient reference device 700 to a patient support (e.g., Mayfield® head holder or patient bed), such that the relationship between the patient reference device 700 and the patient is fixed.

The body 702 may also be configured to enable a sterile cover to be attached to cover the tracking markers 704 and body 702. The sterile cover (not shown) may be transparent to enable detection of the tracking markers 704 (and optionally the feature 706) through the sterile cover. The patient reference device 700 may itself be sterilisable and/or disposable.

There may be at least three tracking markers 704 supported on the first side, and another at least three tracking markers 704 supported on the second side of the body 702. By providing tracking markers 704 on opposing sides of the body 702, this configuration may help to ensure that a sufficient number of tracking markers 704 is detectable by a tracking system, regardless of the direction in which the tracking system is positioned to capture tracking data. For example, the patient may be in a prone (i.e., face down), lateral (i.e., face sideways) or supine (i.e., face up) position. In order to capture the patient's face, the apparatus 500 should be positioned above the patient in a prone position, beside the patient in a lateral position, or below the patient in a supine position. Having tracking markers 704 on both sides of the patient reference device 700 means that the tracking markers 704 are detectable by the first tracking system 506 on the apparatus 500 in each case. Further, the display 510 on the apparatus 500 may be rotatable or flippable, so that the display 510 is easily viewable by a user even when the apparatus 500 is positioned to capture the patient's face from below.

Figure 8:
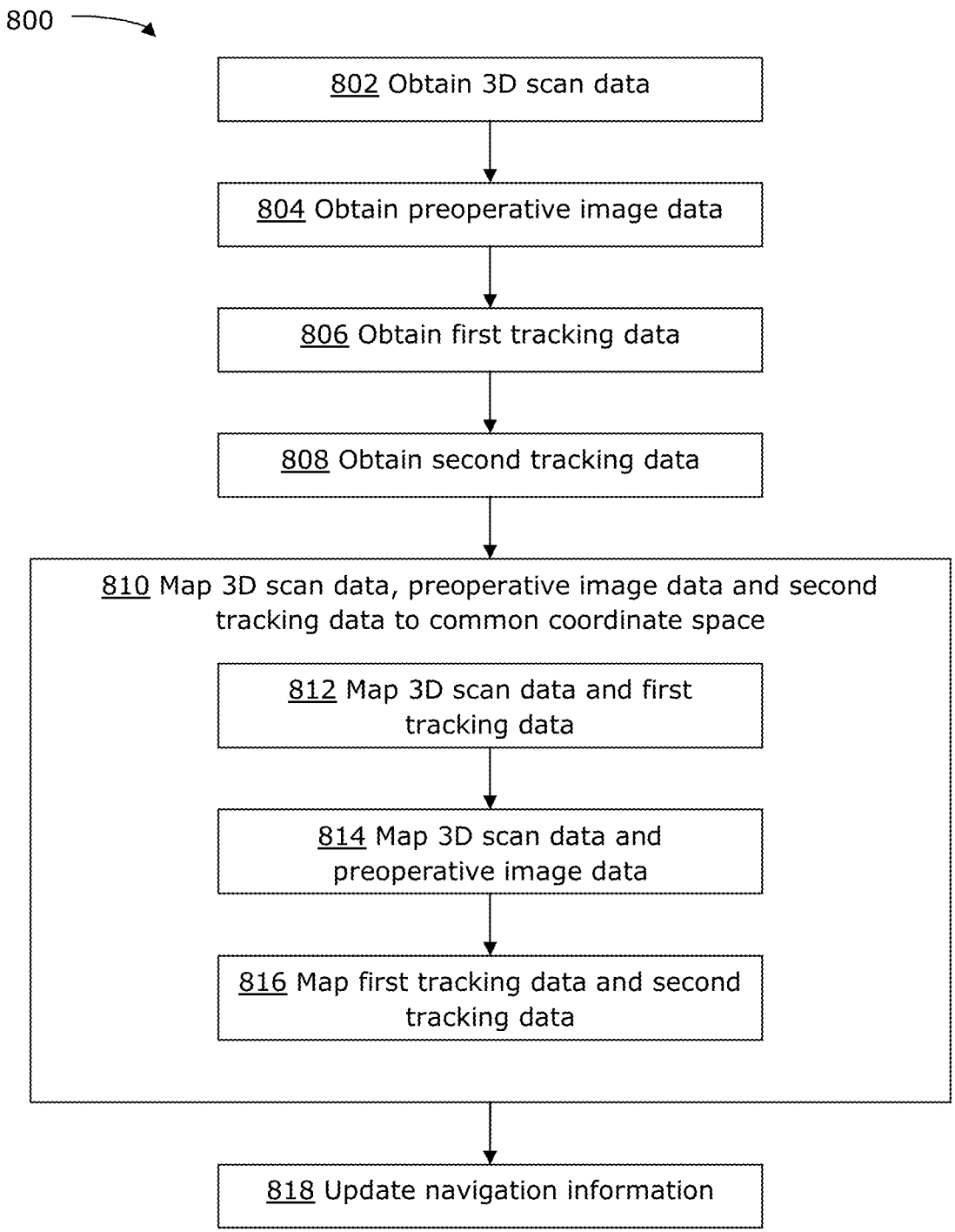
FIG. 8 is a flowchart illustrating an example method for patient registration.

FIG. 8 is a flowchart illustrating an example method 800 for performing patient registration. The method 800 may be performed using the apparatus 500 described above, for example using the calibration object 600 and using the patient reference device 700 described above. In other examples, the method 800 may be performed without using the apparatus 500, calibration object 600 or patient reference device 700 described above.

At 802, 3D scan data for the patient surface is obtained. For example, the 3D scan data can be obtained from the 3D scanner 502 scanning at least a portion of the patient that is relevant to the medical procedure. In the case of a neural procedure, the 3D scan data may be a 3D scan of the patient's face. The 3D scan data may be obtained as a set of points, as a mesh, as a 3D surface or as a 3D point cloud. The 3D scan data is obtained in a 3D scan coordinate space. In some examples, 3D scan data may be obtained using photogrammetry, or any other suitable technique.

At 804, preoperative image data is obtained. This may involve loading saved medical image data, such as preoperative image data saved during a previous scan of at least a portion of the patient including the patient surface scanned in the 3D scan data. At this stage, or later one, a 3D imaging surface may be extracted from the imaging volume of the preoperative image data. The preoperative image data may be MR image data, CT image data, positron emission topography (PET) image data, contrast-enhanced CT image data, X-ray image data, or ultrasound image data, among others. The preoperative image data is in a preoperative image coordinate space.

At 806, first tracking data is obtained. The first tracking data may be obtained from the first tracking system 506 that is coupled to the 3D scanner 502. The first tracking data is obtained for a patient reference device, such as the patient reference device 700 described above. The first tracking data is in a first tracking coordinate space.

The 3D scan data and the first tracking data may be obtained simultaneously, using the apparatus 500 for example. For example, the 3D scan data and the first tracking data may have the same timestamp. The user may use the display 510 on the apparatus 500 to position and orient the apparatus 500 such that the patient surface and patient reference device are both in view, to ensure that the 3D scanner 502 and the first tracking system 506 is able to obtain the 3D scan data and the first tracking data simultaneously. The display 510 may also provide additional visual feedback for positioning the apparatus 500. For example, the image on the display 510 may be given a red hue if the tracking markers (e.g., at least three tracking markers) of the patient reference device are not within view of the first tracking system 506. In some examples, positioning of the apparatus 500 to capture this data may be aided by the distance sensor 508 and the distance indicator 516. For example, the distance indicator 516 may provide a visual indication (e.g., flashes red or green) when the 3D scanner 502 is at a suitable scanning distance from the patient surface. In some examples, after the 3D scan data is captured, a low-resolution preview of the captured 3D surface may be displayed on the display 510 so that the user can verify that the desired patient surface has been scanned.

At 808, second tracking data is obtained. The second tracking data may be provided by the second tracking system, such as the overall tracking system 204 for the navigation system 200. The second tracking data also captures the patient reference device. Thus, the patient reference device may serve as a common reference coordinate for the first and second tracking data. The second tracking data is in a second tracking coordinate space.

802, 804, 806 and 808 may be performed in any order; however, 802 and 806 is generally performed simultaneously, such that the data in the 3D scan data and the data in the first tracking data are obtained at the same time points. It is not necessary for the first and second tracking data to be obtained at the same time points. The data obtained at each of 802, 804, 806 and 808 are all in different independent coordinate systems.

At 810, the 3D scan data, preoperative image data and second tracking data are mapped (or co-registered) to a common coordinate space. This is done by mapping the different sets of data to each other, for example by performing 812, 814 and 816.

At 812, the 3D scan data and first tracking data are mapped to each other. This may be performed using a transformation that relates the 3D scan coordinate space and the tracking coordinate space to each other. The transformation may have been determined based on a prior calibration, for example as described above. The mapping may be performed for 3D scan data and first tracking data that are obtained simultaneously (i.e., at the same time point).

At 814, the 3D scan data and the preoperative image data are mapped to each other. This may be performed using a surface matching algorithm that may match a 3D surface from the 3D scan data with a 3D surface extracted from preoperative volumetric image data (e.g., MR or CT image data). Any suitable method may be used to perform surface matching. Techniques that may be used for surface matching include cropping of the scanned 3D surface to remove regions that should not be included (e.g., if the 3D scan data captured intubation tubes, the tubes should be excluded from surface matching), manual selection of points to help initialize surface matching, and/or automatic calculation of iterative closest point (ICP) to align and match the surfaces.

At 816, the first tracking data and second tracking data are mapped to each other. This may be performed based on the common reference coordinate provided by the patient reference device, which is captured in both the first and second tracking data. For example, a transformation may be calculated, using the common reference coordinate, to map the first and second tracking data to each other.

812, 814 and 816 may be performed in any order, and may be performed in parallel. After 812, 814 and 816 have been performed, the 3D scan data has been mapped to the first tracking data, the 3D scan data has been mapped to the preoperative image data, and the first tracking data has been mapped to the second tracking data. The result is that the 3D scan data, preoperative image data and second tracking data are all mapped to a common coordinate space, so that these sets of data are all co-registered to each other.

At 818, the registration data of the navigation system is updated based on the mapping performed at 810. For example, the transformations calculated at 810 may be saved in the control and processing unit 300 of the navigation system 200. This registration data may be used during the medical procedure to enable the 3D scan data, preoperative image data and intraoperative tracking data by the second tracking system to be displayed together (e.g., as visual overlays), to provide navigational information to the surgeon during the procedure.

The method 800 may be performed by the control and processing unit 300 of the navigation system 200. In some examples, at least some of the method 800 may be performed by an on-board processing unit of the apparatus 500.

The approaches mentioned above may be useful for contactless registration of a patient for a medical procedure. Using an example of the methods and/or apparatuses disclosed, a patient may not need an imaging scan on the day of the medical procedure resulting in eliminating some radiation dosage and possible time and/or cost savings. Problems with shifting of fiducial markers on the patient skin or errors arising from deformation of the patient skin when obtaining touch points may also be avoided.

While the example of an optical tracking system is used, the first and/or second tracking system may include any one of an optical tracking system, an electromagnetic tracking system, and a radio frequency tracking system with appropriate markers being substituted.

Although the above discussion refers to the surgeon as being the user who controls and uses the examples of the present disclosure, it should be understood that the present disclosure is not limited to any specific user. In some examples, there may be a plurality of users involved.

While some embodiments or aspects of the present disclosure may be implemented in fully functioning computers and computer systems, other embodiments or aspects may be capable of being distributed as a computing product in a variety of forms and may be capable of being applied regardless of the particular type of machine or computer readable media used to actually effect the distribution.

At least some aspects disclosed may be embodied, at least in part, in software. That is, some disclosed techniques and methods may be carried out in a computer system or other data processing system in response to its processor, such as a microprocessor, executing sequences of instructions contained in a memory, such as read-only memory (ROM), volatile random access memory (RAM), non-volatile memory, cache or a remote storage device.

A computer readable storage medium may be used to store software and data which when executed by a data processing system causes the system to perform various methods or techniques of the present disclosure. The executable software and data may be stored in various places including for example ROM, volatile RAM, non-volatile memory and/or cache. Portions of this software and/or data may be stored in any one of these storage devices.

Examples of computer-readable storage media may include, but are not limited to, recordable and non-recordable type media such as volatile and non-volatile memory devices, ROM, RAM, flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

Furthermore, at least some of the methods described herein may be capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

At least some of the elements of the systems described herein may be implemented by software, or a combination of software and hardware. Elements of the system that are implemented via software may be written in a high-level procedural language such as object oriented programming or a scripting language. Accordingly, the program code may be written in C, C++, J++, or any other suitable programming language and may comprise modules or classes, as is known to those skilled in object oriented programming. At least some of the elements of the system that are implemented via software may be written in assembly language, machine language or firmware as needed. In either case, the program code can be stored on storage media or on a computer readable medium that is readable by a general or special purpose programmable computing device having a processor, an operating system and the associated hardware and software that is necessary to implement the functionality of at least one of the embodiments described herein. The program code, when read by the computing device, configures the computing device to operate in a new, specific and predefined manner in order to perform at least one of the methods described herein. While the teachings described herein are in conjunction with various embodiments for illustrative purposes, it is not intended that the teachings be limited to such embodiments. On the contrary, the teachings described and illustrated herein encompass various alternatives, modifications, and equivalents, without departing from the described embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

The invention claimed is:

1. A contactless method of registering a patient for a medical procedure using a medical navigation system, the method comprising mapping 3D scan data of a patient surface in a 3D scan coordinate space, preoperative image data in a preoperative image coordinate space, and tracking data in a tracking coordinate space to a common coordinate space by:
mapping the 3D scan data and other tracking data to each other using a transformation, the transformation being determined based on a calibration relating the 3D scan coordinate space and the tracking coordinate space;
mapping the 3D scan data and the preoperative image data to each other using a surface matching algorithm, using the surface matching algorithm comprising: matching a 3D surface from the 3D scan data with a 3D surface extracted from preoperative volumetric image data; cropping the 3D surface to exclude at least one unintended region; and selecting a point to initialize surface matching and automatically calculating an iterative closest point (ICP), thereby aligning and matching the 3D surface from the 3D scan data with the 3D surface extracted from preoperative volumetric image data; and
mapping the tracking data and the other tracking data to each other based on tracking of a patient reference device.

2. The method of claim 1, wherein mapping the 3D scan data of the patient surface in the 3D scan coordinate space the 3D scan data comprises mapping 3D scan data obtained at a given time, wherein mapping the tracking data in a tracking coordinate space comprises data mapping the tracking data obtained at the same given time, and wherein mapping the 3D scan data and the tracking data to each other comprises performing mapping between respective 3D scan data and the tracking data obtained at the same given time.

3. The method of claim 1, further comprising performing the calibration to relate the 3D scan coordinate space and the tracking coordinate space to each other by: obtaining 3D scan calibration data of a calibration device; obtaining tracking calibration data of the calibration device; and calculating the transformation to map the 3D scan calibration data and the tracking calibration data to each other.

4. The method of claim 3, wherein the 3D scanner and a tracking system are in fixed spatial relationship with each other, and wherein performing the calibration comprises performing the calibration prior to obtaining the 3D scan data of the patient surface.

5. The method of claim 1, wherein mapping 3D scan data of the patient surface in a 3D scan coordinate space comprises mapping 3D scan data of the patient surface comprising a surface of a patient's head in one position of prone, lateral, and supine.

6. The method of claim 1, wherein mapping the tracking data and the other tracking data to each other based on tracking of the patient reference device comprises mapping the tracking data and the other tracking data to each other based on tracking of the patient reference comprising: a body having a first side and an opposing second side; at least three tracking markers supported on the first side; and at least another three tracking markers supported on the second side, wherein the tracking markers are trackable by the first and second tracking systems.

7. The method of claim 1 wherein mapping the preoperative image data in a preoperative image coordinate space comprises mapping the preoperative image data comprising at least one of: magnetic resonance (MR) image data, computed tomography (CT) image data, positron emission topography (PET) image data, X-ray image data, and ultrasound image data.

8. A medical navigation system for contactlessly registering a patient for a medical procedure, the medical navigation system comprising a controller in communication with a 3D scanner, a tracking system, and another tracking system, the controller comprising a processor configured to:

map 3D scan data of a patient surface in a 3D scan coordinate space, preoperative image data in a preoperative image coordinate space, and tracking data in a tracking coordinate space to a common coordinate space by:

mapping the 3D scan data and other tracking data to each other using a transformation, the transformation being determined based on a calibration relating the 3D scan coordinate space and the tracking coordinate space;

mapping the 3D scan data and the preoperative image data to each other using a surface matching algorithm, using the surface matching algorithm comprising: matching a 3D surface from the 3D scan data with a 3D surface extracted from preoperative volumetric image data; cropping the 3D surface to exclude at least one unintended region; and selecting a point to initialize surface matching and automatically calculating an iterative closest point (ICP), thereby aligning and matching the 3D surface from the 3D scan data with the 3D surface extracted from preoperative volumetric image data; and map the tracking data and the other tracking data to each other based on tracking of a patient reference device.

9. The system of claim 8, wherein the processor is further configured to: map the 3D scan data of the patient surface in the 3D scan coordinate space the 3D scan data by mapping 3D scan data obtained at a given time, map the tracking data in a tracking coordinate space comprises data by mapping the tracking data obtained at the same given time, and map the 3D scan data and the tracking data to each other by performing mapping between respective 3D scan data and the tracking data obtained at the same given time.

10. The system of claim 8, wherein the processor is further configured to: perform the calibration to relate the 3D scan coordinate space and the tracking coordinate space to each other by: obtaining 3D scan calibration data of a calibration device; obtaining tracking calibration data of the calibration device; and calculating the transformation to map the 3D scan calibration data and the tracking calibration data to each other.

11. The system of claim 10, wherein the 3D scanner and the tracking system are in fixed spatial relationship with each other, and wherein the calibration comprises the calibration prior to obtaining the 3D scan data of the patient surface.

12. The system of claim 8, wherein the processor is further configured to map the 3D scan data of the patient surface in the 3D scan coordinate space by mapping 3D scan data of the patient surface comprising a surface of a patient's head in one position of prone, lateral, and supine.

13. The system of claim 8, wherein the processor is further configured to map the tracking data and the other tracking data to each other based on tracking of the patient reference device comprises mapping the tracking data and the other tracking data to each other based on tracking of the patient reference comprising:

a body having a first side and an opposing second side; at least three tracking markers supported on the first side; and at least another three tracking markers supported on the second side, wherein the tracking markers are trackable by the first and second tracking systems.

14. The system of claim 8, wherein the processor is further configured to map the preoperative image data in a preoperative image coordinate space by mapping the preoperative image data comprising at least one of: magnetic resonance (MR) image data, computed tomography (CT) image data, positron emission topography (PET) image data, X-ray image data, and ultrasound image data.

15. A method of providing a medical navigation system for contactlessly registering a patient for a medical procedure, the method comprising providing a controller in communication with a 3D scanner, a tracking system, and another tracking system, providing the controller comprising providing a processor configured to:

map 3D scan data of a patient surface in a 3D scan coordinate space, preoperative image data in a preoperative image coordinate space, and tracking data in a tracking coordinate space to a common coordinate space by:

mapping the 3D scan data and other tracking data to each other using a transformation, the transformation being determined based on a calibration relating the 3D scan coordinate space and the tracking coordinate space;

mapping the 3D scan data and the preoperative image data to each other using a surface matching algorithm, using the surface matching algorithm comprising: matching a 3D surface from the 3D scan data with a 3D surface extracted from preoperative volumetric image data; cropping the 3D surface to exclude at least one unintended region; and selecting a point to initialize surface matching and automatically calculating an iterative closest point (ICP), thereby aligning and matching the 3D surface from the 3D scan data with the 3D surface extracted from preoperative volumetric image data; and map the tracking data and the other tracking data to each other based on tracking of a patient reference device.

16. The method of claim 15, wherein the processor is further configured to: map the 3D scan data of the patient surface in the 3D scan coordinate space the 3D scan data by mapping 3D scan data obtained at a given time, map the tracking data in a tracking coordinate space comprises data by mapping the tracking data obtained at the same given time, and map the 3D scan data and the tracking data to each other by performing mapping between respective 3D scan data and the tracking data obtained at the same given time.

17. The method of claim 15, wherein the processor is further configured to perform the calibration to relate the 3D scan coordinate space and the tracking coordinate space to each other by: obtaining 3D scan calibration data of a calibration device; obtaining tracking calibration data of the calibration device; and calculating the transformation to map the 3D scan calibration data and the tracking calibration data to each other.

18. The s method of claim 17, wherein the 3D scanner and the tracking system are in fixed spatial relationship with each other, and wherein the calibration comprises the calibration prior to obtaining the 3D scan data of the patient surface.

19. The method of claim 15, wherein the processor is further configured to map the 3D scan data of the patient surface in the 3D scan coordinate space by mapping 3D scan data of the patient surface comprising a surface of a patient's head in one position of prone, lateral, and supine.

20. The method of claim 15,
wherein the processor is further configured to map the tracking data and the other tracking data to each other based on tracking of the patient reference device comprises mapping the tracking data and the other tracking data to each other based on tracking of the patient reference comprising: a body having a first side and an opposing second side; at least three tracking markers supported on the first side; and at least another three tracking markers supported on the second side,
wherein the tracking markers are trackable by the first and second tracking systems, and
wherein the processor is further configured to map the preoperative image data in a preoperative image coordinate space by mapping the preoperative image data comprising at least one of: magnetic resonance (MR) image data, computed tomography (CT) image data, positron emission topography (PET) image data, X-ray image data, and ultrasound image data.

* * * * *